United States Patent
Zaid et al.

(10) Patent No.: US 11,453,665 B2
(45) Date of Patent: *Sep. 27, 2022

(54) THYMOQUINONE/HARMALINE AND RELATED REACTION PRODUCTS

(71) Applicant: Ankh Life Sciences Limited, Dublin (IE)

(72) Inventors: Gene H. Zaid, Hutchinson, KS (US); Cameron E. West, Hutchinson, KS (US)

(73) Assignee: Ankh Life Sciences Limited, Dublin (IE)

(*) Notice: Subject to any disclaimer, the term of this patent is extended or adjusted under 35 U.S.C. 154(b) by 61 days.

This patent is subject to a terminal disclaimer.

(21) Appl. No.: 16/701,581

(22) Filed: Dec. 3, 2019

(65) Prior Publication Data

US 2020/0102306 A1    Apr. 2, 2020

Related U.S. Application Data

(63) Continuation-in-part of application No. 16/380,279, filed on Apr. 10, 2019, now Pat. No. 10,875,859.

(60) Provisional application No. 62/798,547, filed on Jan. 30, 2019, provisional application No. 62/657,315, filed on Apr. 13, 2018.

(51) Int. Cl.
*C07D 471/04* (2006.01)
(52) U.S. Cl.
CPC .................. *C07D 471/04* (2013.01)
(58) Field of Classification Search
CPC .................................................. C07D 471/04
See application file for complete search history.

(56) References Cited

U.S. PATENT DOCUMENTS

| | | |
|---|---|---|
| 2,616,893 A | 11/1952 | Newby |
| 5,304,658 A | 4/1994 | Terao et al. |
| 5,792,799 A | 8/1998 | Sherman-Gold |
| 6,218,434 B1 | 4/2001 | Crooks et al. |
| 8,391,959 B2 | 3/2013 | Mardor et al. |
| 8,586,629 B2 | 11/2013 | De Groote |
| 8,802,161 B2 | 8/2014 | Mazzio et al. |
| 8,841,264 B2 | 9/2014 | Raederstorff et al. |
| 9,180,155 B2 | 11/2015 | Babish et al. |
| 9,404,130 B2 | 8/2016 | Ajikumar et al. |
| 9,630,899 B1 | 4/2017 | Huang et al. |
| 2015/0037308 A1 | 2/2015 | Ikemoto et al. |

(Continued)

FOREIGN PATENT DOCUMENTS

| | | |
|---|---|---|
| WO | 2016064676 A1 | 4/2016 |
| WO | 2019200107 A1 | 10/2019 |
| WO | 202117850 A1 | 9/2021 |

OTHER PUBLICATIONS

Abukhader, M.M . . . "Thymoquinone in the Clinical Treatment of Cancer: Fact or Fiction?" Pharmacogn Review Jul.-Dec3 2013 7(14):117-120.

(Continued)

*Primary Examiner* — Savitha M Rao
*Assistant Examiner* — Andrew P Lee
(74) *Attorney, Agent, or Firm* — Hovey Williams LLP

(57) ABSTRACT

New compositions of matter useful for the treatment of human diabetes and cancers comprise the reaction products of thymoquinone and harmaline or harmaline-like compounds, such as β-carboline compounds, and the derivatives, solvates, prodrugs, isomers, and tautomers of such compounds.

9 Claims, 7 Drawing Sheets

(56) References Cited

U.S. PATENT DOCUMENTS

2016/0213727 A1 7/2016 Rohlfsen
2021/0276998 A1 9/2021 Zaid et al.

OTHER PUBLICATIONS

Hakkarainen, K.M. et al. "Prevalence and Perceived Preventability of Self-Reported Adverse Drug Events—A Population-Based Survey of 7,099 Adults." PLoS One 8.9 (2013): e73166.

Khader et al. "Thymoquinone: an emerging natural drug with a wide range of medical applications" Iran J Basic Med Sci 2014; 17:950-957.

Mani, S. et al. "Alterations of Chemotherapeutic Pharmocokinetic Profiles by Drug-Drug Interactions." Expert Opin. Drug Metabl. Toxicol 5.2 (2009): 109-130.

Obach, R.S. "Drug-Drug Interactions: An Important Negative Attribute in Drugs." Drugs Today 39.5 (2003): 301-338.

Patel, P.S. et al. "A Study of Potential Adverse Drug-Drug Interactions Among Prescribed Drugs in a Medicine Outpatient Department of a Tertiary Care Teaching Hospital." J. Basic Clin. Pharm. 5.2 (2014): 44-48.

PubChem Compound Summary—Harmaline; found online at https://pubchem.ncbi.nim.nih.gov/compound/3564 on Jun. 10, 2019.

PubChem Compound Summary—Thymoquinone; found online at https://pubchem.ncbi.nim.nih.gov/compound/10281 on Jun. 10, 2019.

Villalta-Romero et al. "Identification of New Snake Venom Metalloproteinase Inhibitors Using Compound Screening and Rational Peptide Design," ACS Med. Chem. Lett. 2012, 3, 540-543; found online at pubs.acs.org/acsmedchemlett.

International Search Report and Written Opinion in PCT/US 19/27002 filed Apr. 11, 2019.

Danziger et al. "Automated site-directed drug design: a general algorithm for knowledge acquisition about hydrogen-bonding regions at protein surfaces," Proc. R. Soc. Lond. 236 (1989), 101-113.

International Search Report and Written Opinion in PCT/US2021/020847, filed Mar. 4, 2021.

THYMOQUINONE/HARMALINE AND RELATED REACTION PRODUCTS

CROSS-REFERENCE TO RELATED APPLICATION

This application is a continuation-in-part of U.S. patent application Ser. No. 16/380,279 filed Apr. 10, 2019, which claims the benefit of two U.S. Provisional Applications, Ser. No. 62/798,547 filed Jan. 30, 2019 and Ser. No. 62/657,315 filed Apr. 13, 2018; each of the above-referenced applications is incorporated herein by reference in its entirety.

BACKGROUND OF THE INVENTION

Field of the Invention

The present invention relates to thymoquinone (TQ) adducts with harmaline and related compounds, which are useful for the treatment of human cancers and diabetes, and corresponding methods for the treatment of human suffering from cancers or other maladies. The invention provides dosage forms for administration to human patients, and methods of formulating and administering such dosage forms to yield improvements in treatment outcomes.

Description of the Prior Art

Diabetes is a disease that occurs when a patient's blood glucose (also called blood sugar) is too high. Blood glucose is main source of energy and is derived from ingested food. Insulin, a hormone made by the pancreas, assists in the absorption of blood glucose by cells, where it is used as an energy source. Patients suffering from diabetes do not make enough insulin, or do not use insulin well. Over time, blood glucose can cause severe health problems, such as heart disease, stroke, kidney disease, eye problems, dental disease, nerve damage, and problems with the extremities. Type I diabetes occurs when the body does not make insulin, and is usually diagnosed in children and young adults. People with Type I diabetes need to take insulin to survive. Type II diabetes occurs when the body does not make or use insulin well. This type of diabetes can occur at any age, but most often is seen in middle-aged and older people. Type II diabetes is the most common version. Diabetes is treated with lifestyle changes, including diet and exercise regimes. Additionally, a wide variety of diabetes drugs have been developed and are widely used.

Cancer is a generic term for a large group of diseases that can affect any part of the body. Other terms used are malignant tumors and neoplasms. One defining feature of cancer is the rapid creation of abnormal cells that grow beyond their usual boundaries, and which can then invade adjoining parts of the body and spread to other organs. This process is referred to as metastasis. Metastases are the major cause of death from cancer.

The transformation from a normal cell into a tumor cell is a multistage process, typically a progression from a pre-cancerous lesion to malignant tumors. These changes are the result of the interaction between a person's genetic factors and three categories of external agents, including:
- physical carcinogens, such as ultraviolet and ionizing radiation
- chemical carcinogens, such as asbestos, components of tobacco smoke, aflatoxin (a food contaminant) and arsenic (a drinking water contaminant)
- biological carcinogens, such as infections from certain viruses, bacteria or parasites.

Some examples of infections associated with certain cancers:
- Viruses: hepatitis B and liver cancer, Human Papilloma Virus (HPV) and cervical cancer, and human immunodeficiency virus (HIV) and Kaposi sarcoma.
- Bacteria: *Helicobacter pylori* and stomach cancer.
- Parasites: schistosomiasis and bladder cancer.

Aging is another fundamental factor for the development of cancer. The incidence of cancer rises dramatically with age, most likely due to a buildup of risks for specific cancers that increase with age. The overall risk accumulation is combined with the tendency for cellular repair mechanisms to be less effective as a person grows older.

Tobacco use, alcohol use, low fruit and vegetable intake, and chronic infections from hepatitis B (HBV), hepatitis C virus (HCV) and some types of Human Papilloma Virus (HPV) are leading risk factors for cancer in low- and middle-income countries. Cervical cancer, which is caused by HPV, is a leading cause of cancer death among women in low-income countries. In high-income countries, tobacco use, alcohol use, and being overweight or obese are major risk factors for cancer.

The most common cancer treatment modalities are surgery, chemotherapy, and radiation treatments. All of these techniques have significant drawbacks in terms of side effects and patient discomfort. For example, chemotherapy may result in significant decreases in white blood cell count (neutropenia), red blood cell count (anemia), and platelet count (thrombocytopenia). This can result in pain, diarrhea, constipation, mouth sores, hair loss, nausea, and vomiting.

Biological therapy (sometimes called immunotherapy, biotherapy, or biological response modifier therapy) is a relatively new addition to the family of cancer treatments. Biological therapies use the body's immune system, either directly or indirectly, to fight cancer or to lessen the side effects that may be caused by some cancer treatments.

During chemotherapies involving multiple-drug treatments, adverse drug events are common, and indeed toxicities related to drug-drug interactions are one of the leading causes of hospitalizations in the US. Obach, R. S. "Drug-Drug Interactions: An Important Negative Attribute in Drugs." *Drugs Today* 39.5 (2003): 301-338. In fact, in any single-month period, one-fifth of all surveyed adults in the USA reported an adverse drug response. Hakkarainen, K. M. et al. "Prevalence and Perceived Preventability of Self-Reported Adverse Drug Events—A Population-Based Survey of 7,099 Adults." *PLoS One* 8.9 (2013): e73166. A large-scale study of adults aged 57-85 found that 29% were taking more than five prescription medications and nearly 5% were at risk of major adverse drug-drug interactions. In the field of oncology, a review of over 400 cancer patients determined that 77% were taking drugs that were considered to have a moderately severe potential for adverse drug interactions, and 9% had major adverse drug interactions. Mani, S. et al. "Alterations of Chemotherapeutic Pharmocokinetic Profiles by Drug-Drug Interactions." *Expert Opin. DrugMetabl. Toxicol* 5.2 (2009): 109-130.

Such interactions are a global health problem, and the WHO has determined that negative drug interactions are leading causes of morbidity and mortality around the world, with up to 7% of all hospitalizations in the US due to negative drug interactions. A recent survey of a single hospital shows that 83% of hospitalized patients were prescribed drug combinations with the potential to cause adverse reactions. Patel, P. S. et al. "A Study of Potential Adverse Drug-Drug Interactions Among Prescribed Drugs in a Medicine Outpatient Department of a Tertiary Care Teaching Hospital." *J. Basic Clin. Pharm.* 5.2 (2014): 44-48.

TQ is a phytochemical compound found in the plant *Nigella sativa*, and is also found in select cultivated *Monarda fistulosa* plants grown and steam distilled. TQ has been used as a medicinal agent, such as an anti-convulsant in pediatric epilepsy, as an anti-inflammatory agent, and as an antioxidant. Additionally, TQ has been investigated for anti-cancer effects against several cancer cell lines and animal models. See, e.g., AbuKhader, M. M. "Thymoquinone in the Clinical Treatment of Cancer: Fact or Fiction?" *Pharmacogn Review.* 2013 July-December 7(14):117-120. Additionally, TQ conjugates with terpenes and fatty acids have also been proposed. Further references include U.S. Pat. Nos. 6,218,434, 8,3931,959, 8,586,629, 8,802,161, 8,841,264, 9,180,155, and 9,404,130; US Patent Publication No. 2016/0213727; and non-patent reference, Khader et al, "Thymoquinone: an emerging natural drug with a wide range of medical applications," *Iran JBasic Med Sci* 2014; 17:950-957.

SUMMARY OF THE INVENTION

The present invention provides compositions which may be used as improved chemotherapeutics for treatment of humans, and especially for treatment of human cancers and diabetes, and corresponding methods for preparing such compositions and use thereof. Generally speaking, the chemotherapeutics of the invention are in the form of reaction products of TQ with harmaline and related compounds, and the derivatives, solvates, prodrugs, isomers, and tautomers thereof. The reaction products can be directly used, or can be modified or derivatized to provide therapeutically effective and pharmaceutically acceptable esters, metal complexes (e.g., Cu, Fe, Zn, Pt, V), and salts.

Thymoquinone, C10H12O2, is identified as CAS #490-91-5, and has a molecular weight of 164.2. It has the structure

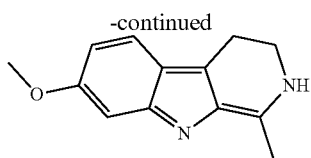

Harmaline (7-methoxy-1-1-methyl-4,9-dihydro-3H-pyrido[3,4-b]indole) is a fluorescent psychoactive alkaloid from the group of harmala alkaloids and β-carbolines, and occurs in various plants, such as *Peganum harmala*. Harmaline is identified as CAS #304-21-2, and exists in two tautomeric forms:

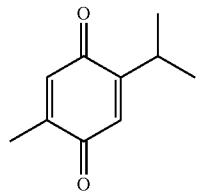

7-methoxy-1-methyl-4,9-dihydro-3H-pyrido[3,4-b]indole
Chemical Formula: $C_{13}H_{14}N_2O$ Exact Mass: 214.11

-continued

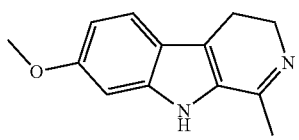

7-methoxy-1-methyl-3,4,-dihydro-2H-pyrido[3,4-b]indole
Chemical Formula: $C_{13}H_{14}N_2O$ Exact Mass: 214.11

As used herein, "harmaline" refers to either or both tautomers.

In another aspect of the invention, compounds related to or similar to harmaline may be used to form the TQ reaction products of the invention.

The invention also provides new methods for treatment of cancers and diabetes (both Type I and Type II) by administration of appropriate quantities of the reaction product compositions hereof. Hence, the compositions are particularly designed for use in the treatment of cancers and diabetes, and the compositions can be used for the manufacture of medicaments for anti-cancer and anti-diabetes therapeutic applications. In addition, the invention provides compositions for the treatment of cancers and diabetes comprising administering therapeutically effective amounts of the new compositions, prepared by processes known per se, with a pharmaceutically acceptable carrier.

A "chemotherapeutic," "chemotherapeutic agent," or simply "therapeutic agent," as used herein refers to one or more of the reaction products of TQ and harmaline described herein as useful in the treatment of human conditions, especially human cancers and diabetes. Chemotherapeutics may be cytostatic, selectively toxic or destructive of cancerous tissue and/or cells, including cancer stem cells, but also include indiscriminately cytotoxic compounds used in cancer treatments.

A study of the reaction products of the invention reveals that certain of the products are isomers and have a molecular weight of approximately 378, or, in dehydrated forms, about 360. Still further, other reaction products have molecular weights of about 542 and, in oxidized forms, about 540. All molecular weights referred to herein are approximate, meaning that the listed molecular weights are +/−5 weight units. Also, the molecular weights of the reaction product derivatives (e.g., reduction products produced by hydrogenation, esters, or salts) would be somewhat different; such weights are easily calculated in light of the nature of the derivatives. Hence, the preferred molecular weights recited herein are for the non-derivatized versions of the reaction products.

DETAILED DESCRIPTION OF THE PREFERRED EMBODIMENTS

Figure 1:
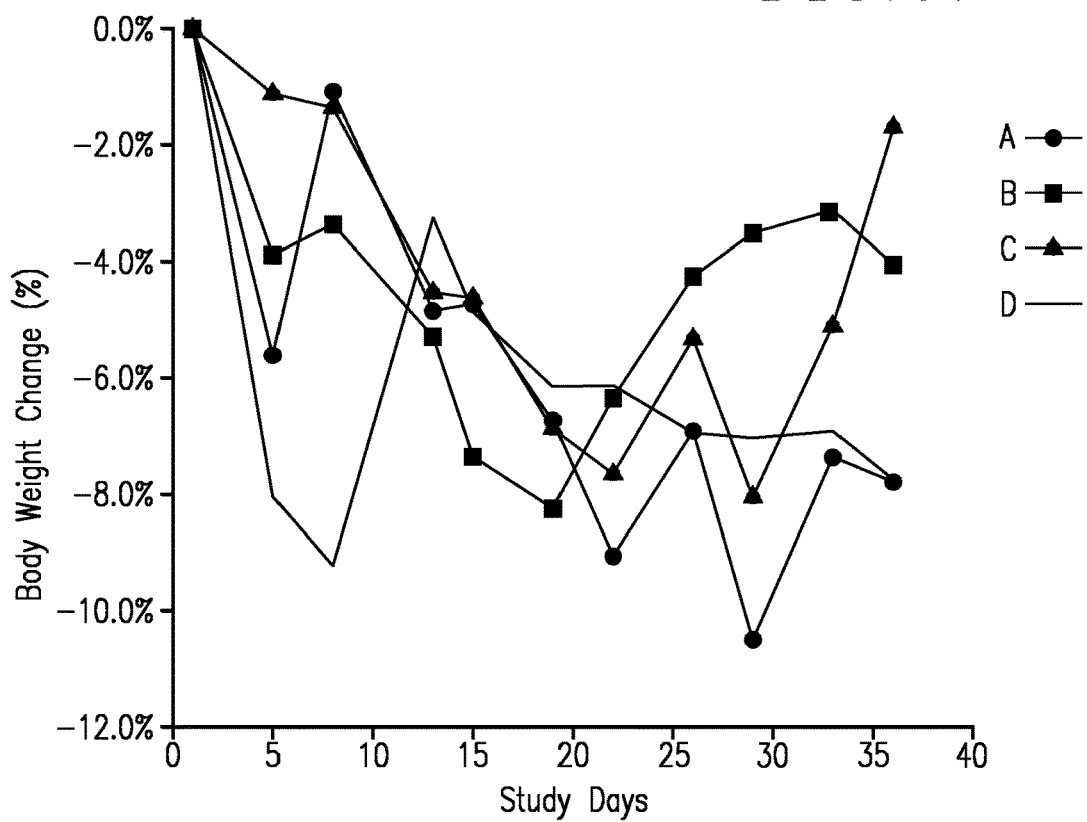
FIG. 1 is a graph illustrating the body weight effect of a reaction product in accordance with the invention, as set forth in Example 2.

The therapeutic agents of the invention are used in therapeutically effective amounts, i.e., amounts that will elicit the biological or medical response of a tissue, system, or subject that is being sought, and in particular to elicit some desired therapeutic effect against a variety of human diseases, and especially cancers and diabetes; in the case of cancers, the agents operate by preventing and/or inhibiting proliferation and/or survival of cancerous cells, including cancer stem cells, and/or by slowing the progression of cancers. Those skilled in the art recognize that an amount may be considered therapeutically effective even if the condition is not totally eradicated or prevented, but it or its symptoms and/or effects are improved or alleviated partially in the subject. Of course, the appropriate makeup of the agents hereof and dosing regimens using such agents will depend on the particular cancer or diabetes being treated, the extent of the disease, and other factors related to the patient as determined by those skilled in the art. Hence, the terms "therapeutic" or "treat," as used herein, refer to products or processes in accordance with the invention that are intended to produce a beneficial change in an existing condition (e.g., cancerous tissue, tumor size, metastases, etc., and the amelioration of diabetes symptoms) of a subject, such as by reducing the severity of the clinical symptoms and/or effects of the condition, and/or reducing the duration of the symptoms/effects of a subject.

Additional ingredients may be included with the chemotherapeutic agents of the invention for administration to the subject. Such additional ingredients include, other active agents, preservatives, buffering agents, salts, carriers, excipients, diluents, or other pharmaceutically-acceptable ingredients. The active agents that could be included in the compositions include antiviral, antibiotic, or other anticancer compounds; the latter could include the compounds described in PCT publication serial number WO2016/064676, such as curcumin, harmine, and isovanillin, and metabolites, derivatives, isomers, tautomers, esters, complexes and salts of any of the foregoing.

The therapeutic agents of the invention give significant and unexpected therapeutic results, particularly in the context of anti-cancer and anti-diabetes results. In use, a therapeutically effective amount of an agent or composition in accordance with the invention is administered to a subject in need thereof. Such may comprise a single unit dosage or, more usually, periodic (e.g., daily) administration of lower dosages over time.

The dosages may be administered in any convenient manner, such as by oral, rectal, nasal, ophthalmic, parenteral (including intraperitoneal, gastrointestinal, intrathecal, intravenous, cutaneous (e.g., dermal patch), subcutaneous (e.g., injection or implant), or intramuscular) administrations. The dosage forms of the invention may be in the form of liquids, gels, suspensions, solutions, or solids (e.g., tablets, pills, or capsules). Moreover, therapeutically effective amounts of the agents of the invention may be co-administered with other chemotherapeutic agent(s), where the two products are administered substantially simultaneously or in any sequential manner.

Levels of dosing using the compositions of the invention are quite variable owing to factors such as the patient's age, patient's physical condition, the type of condition(s) being treated (e.g., specific cancer(s) or diabetes), and the severity of the conditions. In general, however, regardless of the dosage form or route of administration employed, such as liquid solutions or suspensions, capsules, pills, or tablets, via oral, parenteral, or injection, the compositions should be dosed of from about 5 to 2000 mg per day, and more usually from about 100-800 mg per day. Such dosages may be based on a single administration per day, but more usually multiple administrations per day.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

As used herein, pharmaceutically acceptable salts with reference to the reaction products of the present invention mean salts of the reaction products which are pharmaceutically acceptable, i.e., salts which are useful in preparing pharmaceutical compositions that are generally safe, non-toxic, and neither biologically nor otherwise undesirable and are acceptable for human pharmaceutical use, and which possess the desired degree of pharmacological activity. Such pharmaceutically acceptable salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts Properties, and Use*, P. H. Stahl & C. G. Wermuth eds., ISBN 978-3-90639-058-1 (2008).

In preparing the reaction product compositions of the invention, use should be made of ingredients of relatively high purity, typically at least about 90% by weight pure, and more preferably at least about 98% by weight pure. The use of naturally occurring sources for the ingredients is generally not appropriate or desirable, because these naturally occurring products contain relatively small amounts of the desired components and/or have potentially interfering compounds therein. Use of low-purity ingredients often leads to little or no reaction products in accordance with the invention.

Thus, the preferred starting compounds or components of the invention are either synthetically derived or derived from one or more naturally occurring product(s) which have been significantly modified so as to contain at least about 90% by weight (more preferably at least about 98% by weight) of the desired component. As used herein, "synthetically derived" means that the component in question was synthesized using specific starting ingredients and one or more chemical and/or biological reactions to obtain substantially pure compounds. Modification of naturally occurring products may involve extractions, or any other physical or chemical steps to achieve the desired end product.

One technique for preparing the TQ-harmaline reaction products is to mix together solid particulate TQ and harmaline or a similar harmaline-like compound, followed by the addition of a non-interfering solvent, especially organic solvents such as ethanol, or a 90% ethanol/10% dimethyl sulfoxide (DMSO) mixture to the particulates, and allowing the mixture to stand for 24 hours at room temperature. More broadly, the weight ratio of TQ:harmaline should range from about 0.5:1 to 25:1, more preferably from about 0.7:1 to 6:1, and most preferably from about 1.5:1 to 3:1. The most preferred weight ratio is 2:1. In terms of weight amounts, the amount of TQ should range from about 25-95% by weight, and the weight of amount of harmaline should be from about 5-75% by weight, with the total weight of these ingredients taken as 100% by weight. In most cases, however, it is preferred that the amount of TQ be present in a weight excess relative to the amount of harmaline or like compound.

As noted, the TQ and harmaline or a harmaline-like compound are usually mixed with an organic solvent, such as a C1-C4 lower alcohol (e.g., ethanol) and/or DMSO, and allowed to stand for a period (typically from about 12 hours-4 weeks) at a temperature ranging from about 20-60° C. The amount of solvent is quite variable and can range from about 10-100 mg/mL.

The production of effective esters, metal complexes, and pharmaceutically acceptable salts is quite straightforward and well within the skill of the art. For example, salts may be formed by reaction with inorganic or organic acids.

TQ/Harmaline Reaction Products

An analysis of the reaction products reveals that some products described below have molecular weights of about 378, and which may exist in equilibrium with dehydrated versions having molecular weights of about 360 (all molecular weights reported herein were derived using conventional liquid chromatography/mass spectrometry techniques). Structures I-VII below illustrate various forms of these reaction products, where Structures I-IV are isomers, and Structure VII is a dehydrated version of Structure VI.

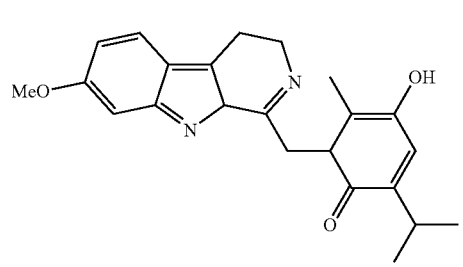

I 4-hydroxy-2-isopropyl-6-((7-methoxy-4,9a-dihydro-3H-pyrido[3,4-b]indol-1-yl)methyl)-5-methylcyclohexa-2,4-dien-1-one
Chemical Formula: $C_{23}H_{26}N_2O_3$
Exact Mass: 378.19

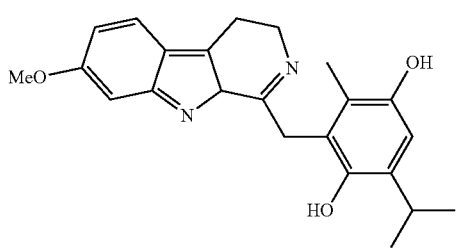

II 5-isopropyl-3-((7-methoxy-4,9a-dihydro-3H-pyrido[3,4-b]indol-1-yl)methyl)-2-methylbenzene-1,4-diol
Chemical Formula: $C_{23}H_{26}N_2O_3$
Exact Mass: 378.19

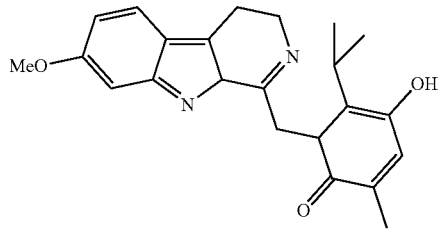

4-hydroxy-5-isopropyl-6-((7-methoxy-4,9a-dihydro-3H-pyrido[3,4-b]indol-1-yl)methyl)-2methylcyclohexa-2,4-dien-1-one
Chemical Formula: $C_{23}H_{26}N_2O_3$
Exact Mass: 378.19
Molecular Weight: 378.47

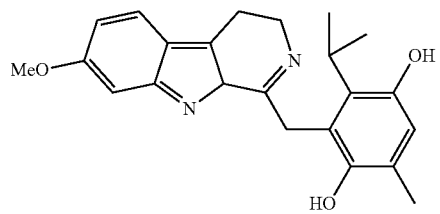

2-isopropyl-3-((7-methoxy-4,9a-dihydro-3H-pyrido[3,4-b]indol-1-yl)methyl)-5-methylbenzene-1,4-diol
Chemical Formula: $C_{23}H_{26}N_2O_3$
Exact Mass: 378.19

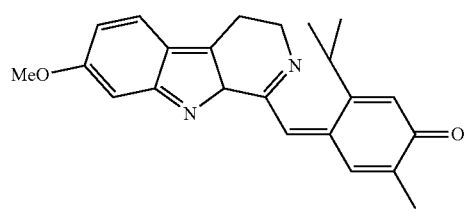

(Z)-5-isopropyl-4-((7-methoxy-4,9a-dihydro-3H-pyrido[3,4-b]indol-1-yl)methylene)-2-methylcyclohexa-2,5-dien-1-one
Chemical Formula: $C_{23}H_{24}N_2O_2$
Exact Mass: 360.18

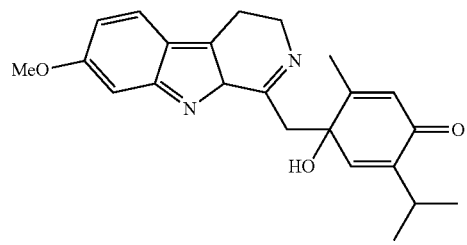

4-hydroxy-2-isopropyl-4-((7-methoxy-4,9a-dihydro-3H-pyrido[3,4-b]indol-1-yl)methyl)-5-methylcyclohexa-2,5-dien-1-one
Chemical Formula: $C_{23}H_{26}N_2O_3$
Exact Mass: 378.19

III

IV

V

VI

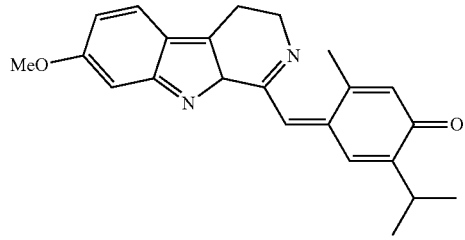

(Z)-2-isopropyl-4-((7-methoxy-4,9a-dihydro-3H-pyrido[3,4-b]indol-1-yl)methylene)-5-methylcyclohexa-2,5-dien-1-one
Chemical Formula: $C_{23}H_{24}N_2O_2$
Exact Mass: 360.18

VII

The above reaction products are characterized by a single thymoquinone moiety and a single harmaline or harmaline-like moiety. These predominate during the initial stages of the reactions. In these reactions, the substituent of the pyridyl ring of harmaline reacts at an unsubstituted carbon atom which is alpha to either of the carbonyl groups of TQ. This phenomenon is illustrated in Structures I-IV above. In another reaction scheme, the substituent of the pyridyl ring of harmaline reacts directly with either of the carbonyl groups of TQ. These types of reactions are illustrated in Structures V-VII above.

The thermodynamic properties of the harmaline and TQ reactants and reaction products I-IV isomers (MW 378) were used to obtain reaction energetics using Density Functional Theory (DFT). Additional calculations were used to determine enthalpy, entropy, and Gibbs free energy values for the reactions. Reaction products II and IV were found to be the most thermodynamically favorable and smaller free energy values. Reaction product II was deemed to be the most stable and had the lowest free energy value. Note that compounds II and IV are characterized by reaction of the pyridyl ring methyl substituent with one of the two unsubstituted carbon atoms alpha to a corresponding carbonyl carbon, and two hydroxyl substituents on the TQ ring.

However, if the reaction mixtures are allowed to set for an extended period of time, e.g., from about 3-30 days, other reaction products having higher molecular weights of about 542, or in oxidized forms, about 540 are formed as the predominant reaction product. These reaction products are characterized by the presence of two thymoquinone moieties and a single harmaline or harmaline-like moiety. These same types of higher molecular weight species can be obtained if, after the initial reaction to yield the 378/360 MW products I-VII, the reaction mixtures are refluxed for a period of from about 30-120 minutes.

In particular, the MW 542 reaction products, and their oxidized MW 540 reaction products, formed by the reaction between thymoquinone and harmaline are set forth below as compounds VIIIA-VIIIF:

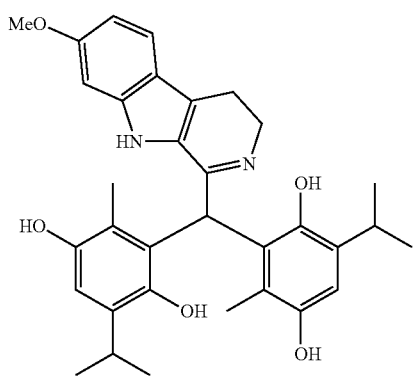

VIIIA
3,3'-((7-methoxy-4,9-dihydro-3H-pyrido[3,4-b]indol-1-yl)methylene)bis(5-isopropyl-2-methylbenzene-1,4-diol)
Chemical Formula: $C_{33}H_{38}N_2O_5$
Exact Mass: 542.28
Molecular Weight: 542.68

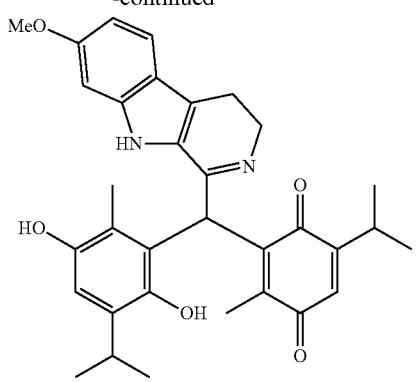

VIIID
3-((2,5-dihydroxy-3-isopropyl-6-methylphenyl)(7-methoxy-4,9-dihydro-3H-pyrido[3,4-b]indol-1-yl)methyl)-5-isopropyl-2-methylcyclohexa-2,5-diene-1,4-dione
Chemical Formula: $C_{33}H_{36}N_2O_5$
Exact Mass: 540.26
Molecular Weight: 540.66

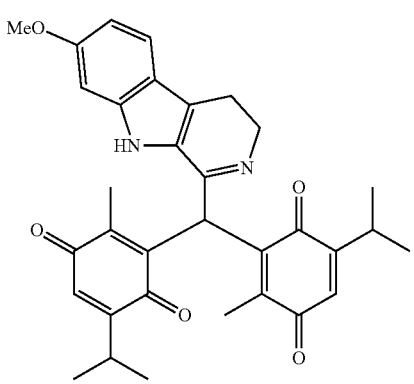

VIIIB
3,3'-((7-methoxy-4,9-dihydro-3H-pyrido[3,4-b]indol-1-yl)methylene)bis(5-isopropyl-2-methylcyclohexa-2,5-diene-1,4-dione)
Chemical Formula: $C_{33}H_{34}N_2O_5$
Exact Mass: 538.25
Molecular Weight: 538.64

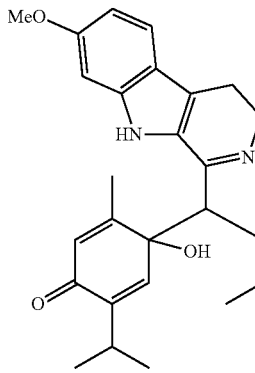

VIIIE
4-((2,5-dihydroxy-3-isopropyl-6-methylphenyl)(7-methoxy-4,9-dihydro-3H-pyrido[3,4-b]indol-1-yl)methyl)-4-hydroxy-2-isopropyl-5-methylcyclohexa-2,5-dien-1-one
Chemical Formula: $C_{33}H_{38}N_2O_5$
Exact Mass: 542.28
Molecular Weight: 542.68

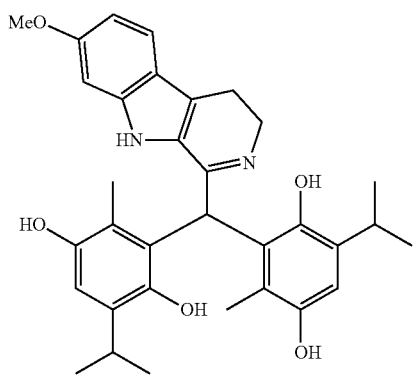

VIIIC
3,3'-((7-methoxy-4,9-dihydro-3H-pyrido[3,4-b]indol-1-yl)methylene)bis(5-isopropyl-2-methylbenzene-1,4-diol)
Chemical Formula: $C_{33}H_{38}N_2O_5$
Exact Mass: 542.28
Molecular Weight: 542.68

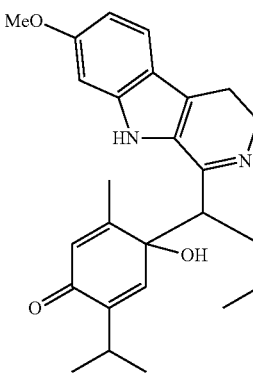

VIIIF
3-((1-hydroxy-5-isopropyl-2-methyl-4-oxocyclohexa-2,5-dien-1-yl)(7-methoxy-4,9-dihydro-3H-pyrido[3,4-b]indol-1-yl)methyl)-5-isopropyl-2-methylcyclohexa-2,5-diene-1,4-dione
Chemical Formula: $C_{33}H_{36}N_2O_5$
Exact Mass: 540.26
Molecular Weight: 540.66

Presently, compounds II and IV above are deemed to be the most active, particularly in the context of diabetes.

Related Harmaline Reactants

Certain similar or related harmaline compounds can be used in the production of the TQ reaction products of the invention, in lieu of or in combination with harmaline. Suitable "harmaline-like" compounds are β-carbolines, and especially compounds of the structure IX

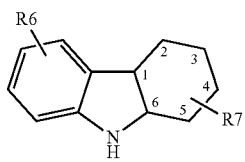

where the right-hand, numbered 6-member fused ring is heterocyclic with a single N atom at any of the positions 2-5, the R6 and R7 substituents may be located at any ring position, and R6 is H or C1-C4 alkoxy (more preferably a C1-C2 alkoxy), and R7 is H, a C1-C4 alkyl (more preferably a C1-C2 alkyl), or a C1-C4 carboxylic acid (more preferably a C1-C2 carboxylic acid).

Representative compounds of this type include harmaline and the following:

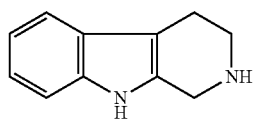

1,2,3,4-Tetrahydro-9H-pyrido[3,4-b]indole (THbC)

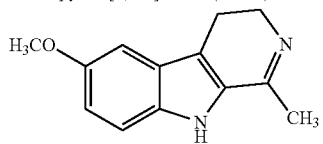

6-Methoxyharmalan

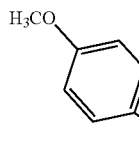

6-Methoxy-1,2,3,4-tetrahydro-9H-pyrido[3,4-b]indole (pinoline)

2,3,4,5-tetrahydro-8-methoxy-1H-pyrido[4,3-b]indole

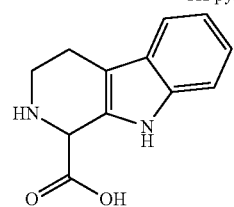

1,2,3,4-tetrahydro-beta-carboline-1-carboxylic acid

The methods of preparing the reaction products using the compounds of Structure IX are the same as those applicable to the preferred TQ/harmaline reaction products. In like manner, the weight ratios of TQ to the Structure IX compounds are the same as those described above in connection with TQ and harmaline, as are the levels of dosing and the types of dosage forms which may be prepared.

Thus, the weight ratio of TQ to the Structure IX compounds in the reaction mixtures should range from about 0.5:1 to 25:1, more preferably from about 0.7:1 to 6:1, and most preferably from about 1.5:1 to 3:1. The most preferred weight ratio of TQ:Structure IX compound(s) is 2:1. In terms of weight amounts, the TQ amount should range from about 25-95% by weight, and the weight of amount of Structure IX compound(s) should be from about 5-75% by weight, with the total weight of these reactants taken as 100% by weight. In most cases, it is preferred that the weight amount of TQ should be present in a weight excess relative to the amount of the Structure IX compound(s).

The TQ and Structure IX compound(s) are usually mixed with an organic solvent, such as a C1-C4 lower alcohol (e.g., ethanol) and/or dimethyl sulfoxide (DMSO), and allowed to stand for a period (typically from about 12 hours-4 weeks) at a temperature ranging from about 20-60° C. The most preferred conditions are the addition of organic solvent at a level of from about 10-100 mg/mL, with standing for 24 hours at room temperature.

The production of effective esters, metal complexes, and pharmaceutically acceptable salts of the TQ/Structure IX compounds, as well as all other compounds within the ambit of the invention, is quite straightforward and well within the skill of the art. For example, salts may be formed by reaction with inorganic or organic acids, as previously described.

Certain preferred reaction products in accordance with the invention are set forth in Structures X and XI below, where Structure X corresponds to the lower MW products and Structure XI corresponds to the higher MW products.

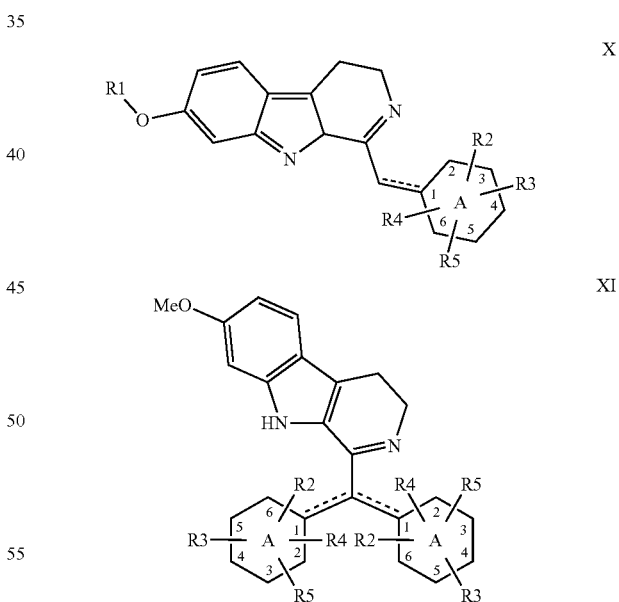

where the six-membered A ring in each of the above structures is either phenyl or cyclohexadiene, the R1-R5 substituents may be attached at any valence-permitted position around the corresponding A rings, R1 is a C1-C4 alkyl group, R2 is H or a C1-C4 alkyl group, R3 and R4 are independently either —OH or =O, R5 is isopropyl, and the dotted bond line refers to the fact that the bond between the 1 position on the A ring and the intermediate CH2 or CH group of the linker between the A ring and the six-membered, N-containing pyridyl ring may be either a single bond or a double bond. In structure XI, the A rings may be the same or different.

EXAMPLES

Example 1

A. Objective/Rationale

This test was designed to evaluate the in vivo activity of the TQ-harmaline reaction product (referred to as "TQ 725"), which was a mixture of compounds I-IV and VI (MW about 378), V and VII (MW about 360), and VIIID and VIIIF (MW about 540), as single agent in the NOD mouse model of diabetes. Subsequent investigations have confirmed that compounds VI and VII are the most active. The female NOD mice show evidence of diabetes onset by age week 12 and 70% presenting with diabetes (non-fasting plasma glucose higher than 250 mg/dl) by age week 20. The significant endpoint is assessment of weekly blood glucose levels.

B. Materials and Methods

1. Test System

| | |
|---|---|
| Species/strain: | NOD/ShiLtJ (Stock No: 001976) |
| Physiological state: | Diabetic |
| Age/weight range at time of receipt: | 8-11 weeks (NOD/ShiLtJ) - 11 weeks preferred if offered by the vendor |
| Number/sex of animals: | 40/Female* |
| Replacement: | Animals were not replaced during the course of the study. |

*Number of mice were reduced to 36 prior to study starting.

2. Animal Housing and Environment

| | |
|---|---|
| Housing: | Individually ventilated microisolator cages |
| Acclimation: | At least 5-7 days |
| Environmental conditions: | Maintained under pathogen-free conditions |
| Food/water: | Ad libitum, Teklad Global Diet ® 2920x irradiated pellets, autoclaved water. |

3. Test Article—TQ 725.

| | |
|---|---|
| Physical description: | Solid taffy |
| Storage conditions: | 4° C. protected from light |

4. Test Article/Vehicle Mixture—TQ 725

| | |
|---|---|
| Dosage forms: | Suspension |
| Dosage preparation/storage: | Suspension of TZ 725 in 10% dimethyl acetamide (DMA) + 90% polyethylene glycol (PEG400)/4° C. protected from light |
| Stability/expiration date: | Prepared fresh prior to dosing |

5. Administration of Test Agent—TQ 725

| | |
|---|---|
| Route and method of administration: | Oral Administration per os (PO) |
| Frequency and duration of dosing: | Daily to end (QD to end) |
| Administered doses: | 100 mg/kg, 200 mg/kg, 400 mg/kg, and 600 mg/kg |
| Administered volume(s): | 10 mL/kg |

6. Standard Agent—Metformin

| | |
|---|---|
| Identity: | Metformin |
| Physical description: | Solid |
| Storage conditions: | Room temperature away from light and moisture |
| Stability/expiration date: | Greater than study duration |

7. Standard Agent/Vehicle Mixture—Metformin

| | |
|---|---|
| Dosage form: | Solution |
| Dosage preparation/storage: | Aqueous solution |
| Stability/expiration date: | Aqueous solutions were stable for the duration of the study, kept at 4° C. |

8. Administration of Standard Agent—Metformin

| | |
|---|---|
| Route and method of administration: | Oral Administration (PO) |
| Frequency and duration of dosing: | Ad libitum, days 1-8 in drinking water; oral gavage daily, days 9-56 |
| Administered doses: | 600 mg/kg |

9. Vehicle Control

| | |
|---|---|
| Identity: | 10% DMA + 90% PEG400 |

10. Vehicle Mixture—Vehicle Control

| | |
|---|---|
| Dosage form: | solution |
| Dosage preparation/storage: | 10% DMA + 90% PEG400 |

11. Administration of Vehicle Control

| | |
|---|---|
| Route and method of administration: | Oral Administration (PO) |
| Administered doses: | 0 mg/kg |
| Administered volume(s): | 10 mL/kg |

12. Experimental Design

| | |
|---|---|
| Study initiation: | At approximately 23 weeks of age, mice were randomized into treatment groups (Day 0) for baseline blood glucose measurements. |
| Randomization method: | Random equilibration of glucose levels and body weights |
| Treatment initiation: | On Day 1, According to Table 1 below. |
| Data Collection: | Body Weights two times weekly; Gross observations daily (negative observations will be recorded) |
| Study Endpoint(s): | 8 Weeks Post Study Initiation |

13. Tissue Collection

In-study collections: Pre-dose; then once weekly for 8 weeks prior to dosing animals Moribund mice will have blood glucose collections prior to sacrifice when possible

| | | | |
|---|---|---|---|
| Tissue: | Blood Glucose | Collection Method: | Tail prick |
| Group(s): | All Groups | Preservation Method: | N/A |
| Samples per group: | All Mice | Analysis Method: | Glucose Meter |

14. Daily Dosing Schedule

TABLE 1

Study Groupings

| Group | N* | Dosing Schedule |
|---|---|---|
| 1. Vehicle Control (PO) | 6 | 10 ml/kg |
| 2. TQ 725(PO) | 6 | 100 mg/kg days 1-27 |
| | | 400 mg/kg days 28-37 |
| | | 600 mg/kg days 38-56 |
| 3. TQ 725 (PO) | 5 | 200 mg/kg days 1-56 |
| 4. Metformin (PO) | 6 | Ad libitim days 1-8 |
| | | 600 mg/kg days 9-56 |

*Number of mice in group.

The pancreatic tissues from the test mice were assayed by conventional insulin staining according to the following ratings: 0—no staining on islet cells; 1—of islets with positive stains, stain cells are minimal in number; 2—of islets with positive stain, stain cells are less than 50% of the cells; 3—of the islets with positive stains, stain cells are greater than 50% of the cells.

The staining data showed a mean value of 0.67 for Group 1, 1.5 for Group 2, 2.40 for Group 3, and 0.50 for Group 4. Thus, the data demonstrated a marked increase insulin staining for the TQ 725 Groups 2 and 3, as compared with the control Group 1 and the Metformin Group 4.

The collected body weight data for the test mice indicated that the Metformin Group 4 weights trended downwardly, whereas the body weights of the Group 3 mice were almost always higher than those of Group 4. The body weight data was not deemed to be a reliable parameter since mice were sacrificed and removed during the course of the test, which effected body weight results.

Figure 2:
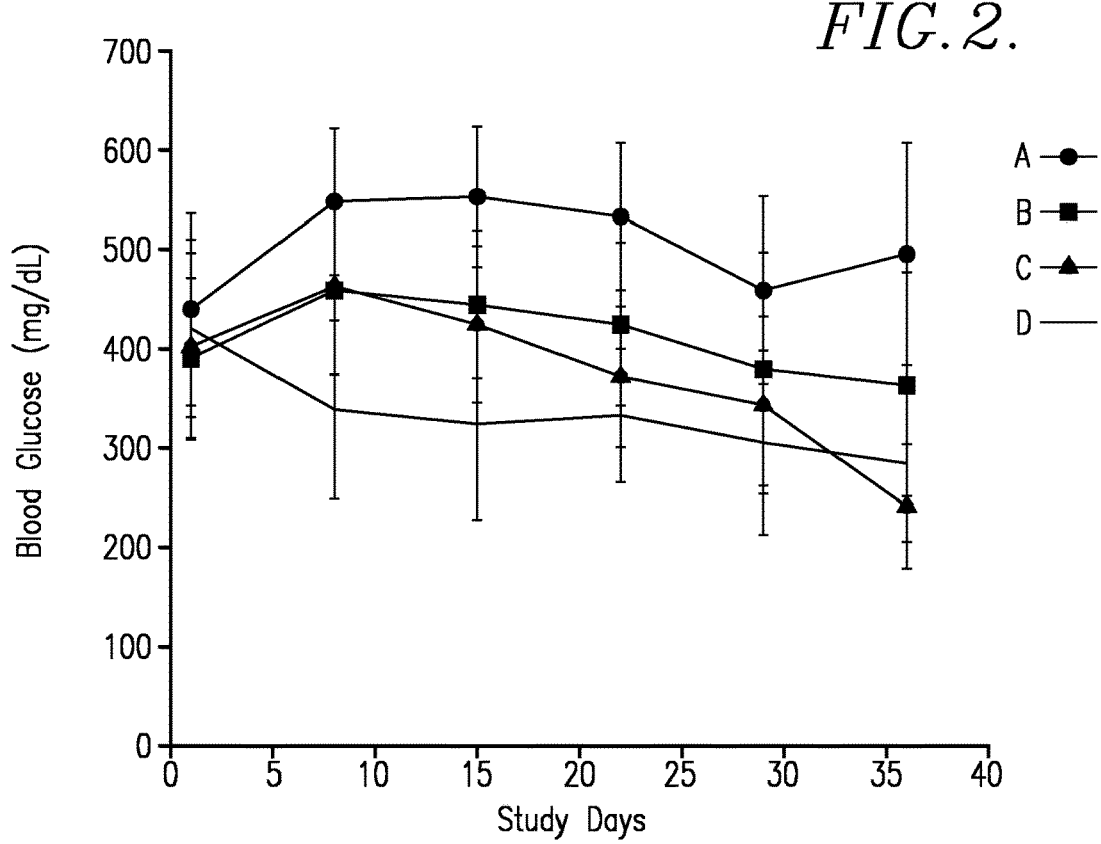
FIG. 2 is a graph illustrating the blood glucose effect of a reaction product in accordance with the invention, as set forth in Example 2.

FIGS. 1 and 2 illustrate the body weight and blood glucose level results collected during the test. In each of these Figures, graph A refers to Group 1, the vehicle control (PO) QD to end; graph B refers to Group 2, 725.001 100 mg/kg days 1-27, followed by 400 mg/kg days 28 to end (PO); graph C refers to Group 3, 725.001 200 mg/kg (PO) QD to end; and graph D refers to Group 4, metformin 600 mg/kg (in H2O) Ad libitum days 1-8, followed by 600 mg/kg (PO) QD days 9 to end.

The Group 3 graph C data was the most significant, in that it illustrated a general decline in blood glucose over the course of the study, with enhanced body weights. The Group 2 graph B data illustrated that the increase in TQ 725 dosage during the course of the test lowered the glucose levels. At about 35 days, the glucose levels of the Group 3 graph C mice fell below those of the Group 4 graph D mice, and this trend continued throughout the remainder of the test.

Example 2

The purpose of this study was to assess the maximum tolerated single dose of the TQ 725 product as a single agent in 27 female non-tumor-bearing SCID beige mice. A stepwise approach was used to determine the single dose tolerability.

The mice were five weeks of age at the time of dosing and had a normal physiological state. The mice were housed in individual, ventilated, microisolator cages under pathogen-free conditions. The mice were fed Ad libitum Teklad Global Diet 2920x eradiated pellets, and autoclaved water. IACUC Protocol #16094 was followed.

The test product was a DMSO solution containing 100 mg/mL of the TQ 725 reaction product stored at 4° C. and protected from light. This test product was used to prepare a dosage form made up of 10% of the DMSO/725 test product, diluted with 90% PEG 400 by gentle hand mixing. The dosage form was stored at 4° C. and protected from light.

The dosage form was administered orally in a single dose. Three groups of 9 mice each acclimated at 7, 8, and 9 days, respectively, were given doses of 50 mg/kg, 75 mg/kg, and 100 mg/kg. One mouse per group was dosed and observed. When no acute tolerability-related adverse clinical signs were noted, the remaining mice of each group were dosed.

The mice were observed over a period of 10 days and daily data of body weight and gross observations were collected. There was only mild body weight loss and no significant tolerability-related clinical observations or death. Therefore, it was concluded that the product was well-tolerated at all of the dose levels tested.

Example 3

In this Example, in vitro cell proliferation assays were performed using: (1) Human Myeloma tumor cell lines; (2) Human Lymphoma tumor cell lines; (3) Solid Human tumor cell lines; and (4) Parental, Lenalidomide resistant and Bortezomib resistant Jeko-1 Mantle cell Lymphoma tumor cell lines. The reaction product tested was the TQ 725 product described above.

Each proliferation assay was carried out as follows. The test cells were plated in growth media using a 384-well microtiter plate at 50 μL volume. The cells were incubated for 24 hours at 37° C. in a humidified incubator. After 24 hours of incubation, the test TQ 725 product was added to the test wells in DSMO solvent, at a concentration ranging of 10.5 mM. Control wells received equal volumes of DSMO, without the reaction product. Following drugging, the cells were incubated for 72 hours at 37° C. in a humidified incubator. After this exposure, 100 μL of a 1:1 mixture of sterile water and CellTiter-Glo® reagent (Promega) was added to each well. The plates were then incubated for 60 minutes at room temperature, followed by recording the luminescence value of each well using a luminometer as a measure of cell proliferation.

The following Table sets forth a summary of the $IC_{50}$ Results.

In Vitro Cell Proliferation Assay
Summary of $IC_{50}$ Results

| Cell Line | Tissue Type | Mean $IC_{50}$ (μM) TQ 725 |
|---|---|---|
| MIA PaCa-2 | Pancreatic | 8.983 |
| ASPC-1 | | 11.62 |
| BxPC-3 | | 10.56 |
| AN3CA | Endometrial | 8.226 |
| HEC-1a | | 18.01 |
| MDA-MB-231 | TNBC | 5.270 |
| MDA-MB-468 | | 5.540 |
| HCC70 | | 18.99 |
| H1975 (EGFR mut) | NSCLC | 7.100 |
| H1650 (EGFR mut) | | 14.29 |
| A2780 | Ovarian | 2.237 |
| A2780CP | | 4.717 |
| RXF-393 | RCC | 6.022 |
| A498 | | 13.85 |
| N87 | Gastric | 9.604 |
| SiHA | Squamous Cell | 40.99 |
| FaDu | | 14.43 |
| DOHH-2 | DLBCL | 4.232 |
| SU-DHL-4 | | 1.168 |

-continued

In Vitro Cell Proliferation Assay
Summary of IC$_{50}$ Results

| Cell Line | Tissue Type | Mean IC$_{50}$ (μM) TQ 725 |
|---|---|---|
| SU-DHL-6 | | 0.7158 |
| OCI-LY3 | | 0.9209 |
| JIM1 | human myeloma | 8.197 |
| KHM-1B | | 4.377 |
| KMM-1 | | 6.118 |
| KMS-11 | | 15.85 |
| KMS-27 | | 7.256 |
| KMS-34 | | 16.91 |
| H929 | | 14.19 |
| L363 | | 12.65 |
| MM.1S | | 4.795 |
| MOLP-8 | | 1.746 |
| Jeko-1 Parental | Mantle Cell Lymphoma | 4.378 |
| Jeko-1 Lenalidomide Resistant | | 8.917 |
| Jeko-1 Bortezomib Resistant | | 5.705 |

Example 4

In this example, two of the compounds in accordance with the invention, referred to as C1 and C2, were identically tested to determine cell cytotoxicities. C1 has a molecular weight of about 378 and is a mixture of compounds I-IV and VI. C2 has molecular weight of about 360 and is a mixture of compounds V and VII. The cell line used was MIN-6 (ATCC CRL-11506) pancreatic beta cells. The cells were seeded into 96-well plates (10$^4$ cells/well) along with Dulbecco's Modified Eagle Medium (DMEM) containing 10% fetal bovine serum, 0.05 mM 2-mercaptoethanol, 100 U/mL penicillin, 100 μg/mL streptomycin, 3.7 g/L NaHCO$_3$, 25 mM glucose, and 200 mM glutamine, with incubation under a humidified atmosphere at 37° C. with 5% C02. After 72 hours of incubation, the cells were treated with compounds C1 and C2, respectively, in 0.5% DMSO at levels of 0.1, 1.0, 10, and 100 μg/mL, and allowed to react overnight. Thereupon, each well was treated with 20 μL of freshly prepared (5 mg/mL) MTT (3-(4,5-dimethylthizol-2-yl)-2,5-diphenyltetrazolium bromide) stock in 1×PBS, followed by an additional hour of incubation. Finally, 100 μL of DMSO was added to each well, and the absorbance was recorded at 570 nm. A control was identically prepared and tested, except that the cells were not treated with either test compound. A positive control of methyl methanesulphonate (1000 μM) was also tested.

Figure 3:
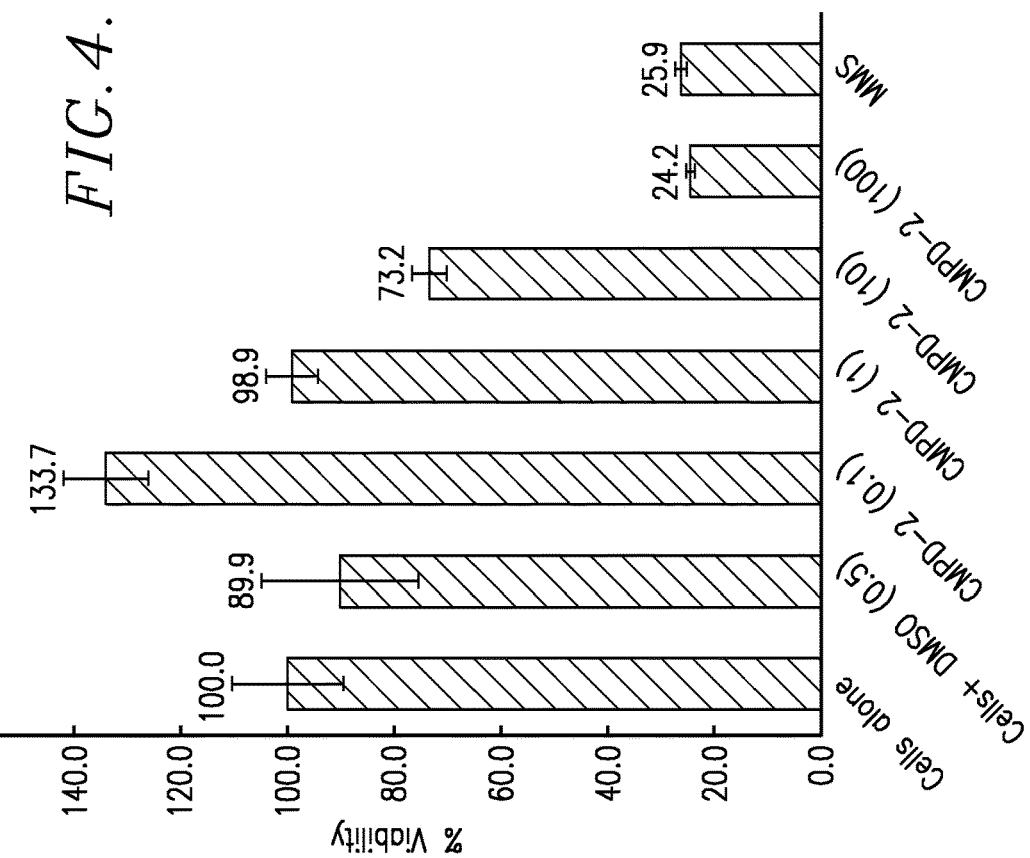
FIG. 3 is a graph illustrating cell cytotoxicity results using one compound in accordance with the invention, as set forth in Example 4.
Figure 4:
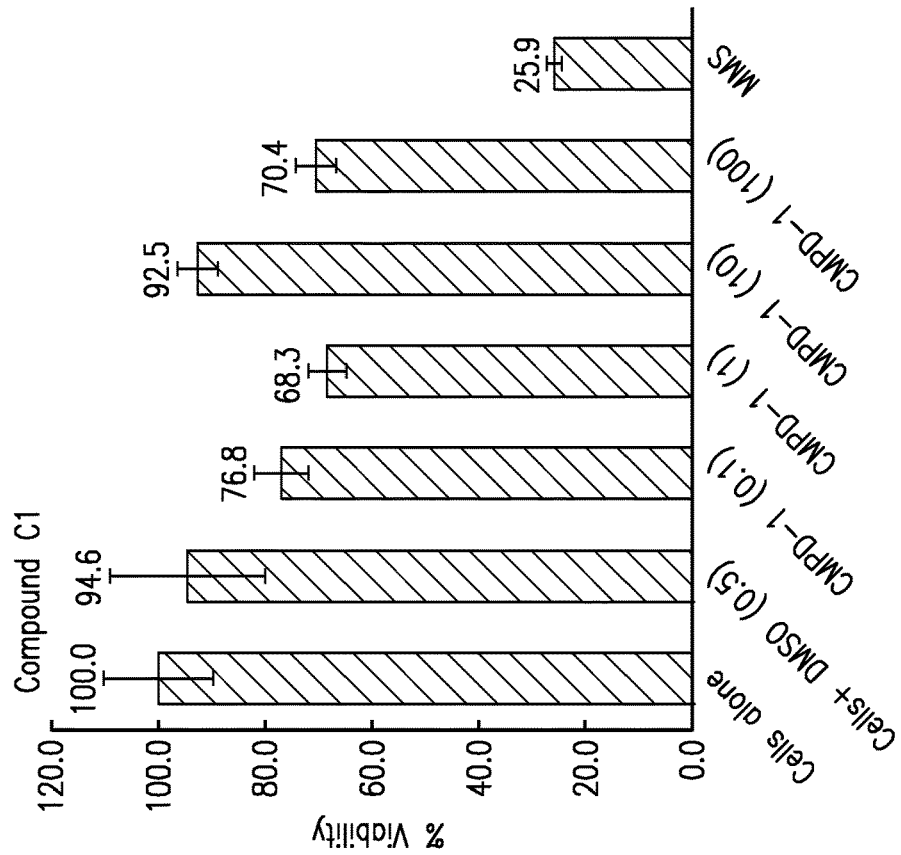
FIG. 4 is a graph illustrating cell cytotoxicity results using another compound in accordance with the invention, as set forth in Example 4.

FIGS. 3 and 4 illustrate the results from this test where the data is presented as % cell viability compared to the cell control. As indicated, compound C1 was not toxic to the MIN-6 cells at tested doses. In the case of compound C2, no toxicity was observed at lower concentrations, but significant cell cytotoxicity towards the MIN-6 cells was visible at 100 μg/mL.

Example 5

In this test, a glucose stimulated insulin secretion assay was performed using the MIN-6 cell line and compounds C1 and C2 of Example 4. The test details and assay conditions are set forth below.

A. Test Details

| | |
|---|---|
| Cell Line | MIN-6 |
| Cell Density | 3 × 10$^4$ cells/well |
| Compounds | C1 |
| | C2 |
| | Diazoxide |
| Solvent | DMSO |
| Test Concentrations | 1.0, 10.0 μg/mL |
| Cell Control | Krebs Ringer Buffer (KRB) containing 0.1% BSA (no glucose) |
| Vehicle Control | 0.5% DMSO |
| Control | Glucose + 0.5% DMSO |
| Test | Glucose + C1 or C2 in DMSO |

B. Assay Conditions

Figure 6:
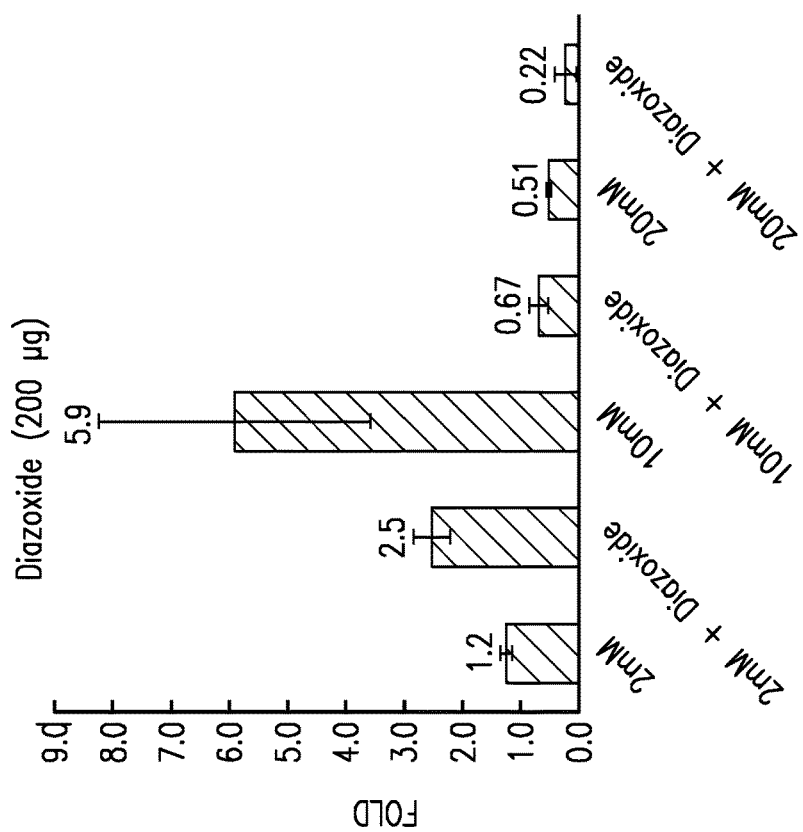
FIG. 6 is a graph illustrating insulin secretion assay results with varying amounts of glucose and diazoxide, as set forth in Example 5.
Figure 5:
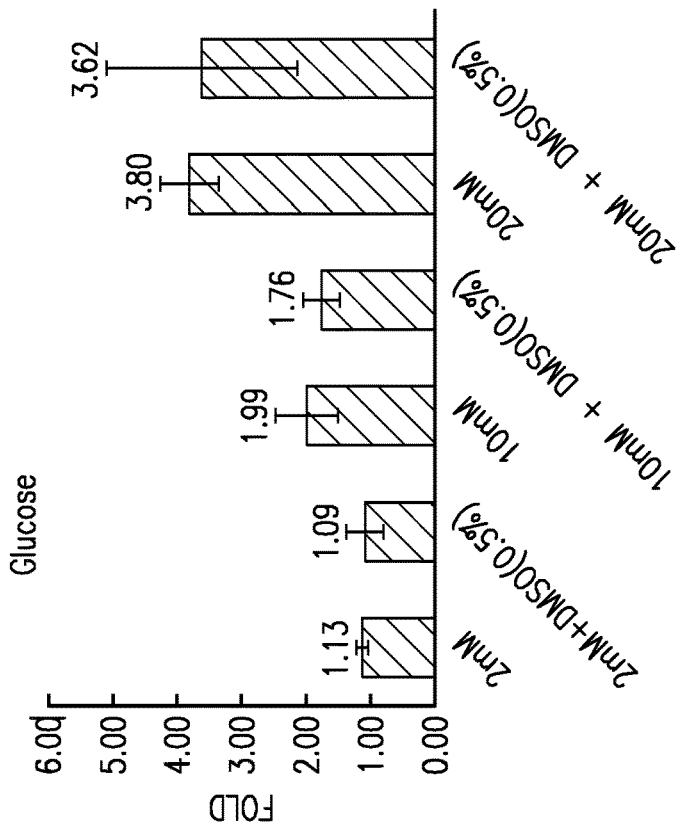
FIG. 5 is a graph illustrating baseline insulin secretion assay results with varying amounts of glucose alone and in conjunction with DMSO, as set forth in Example 5.
Figure 7:
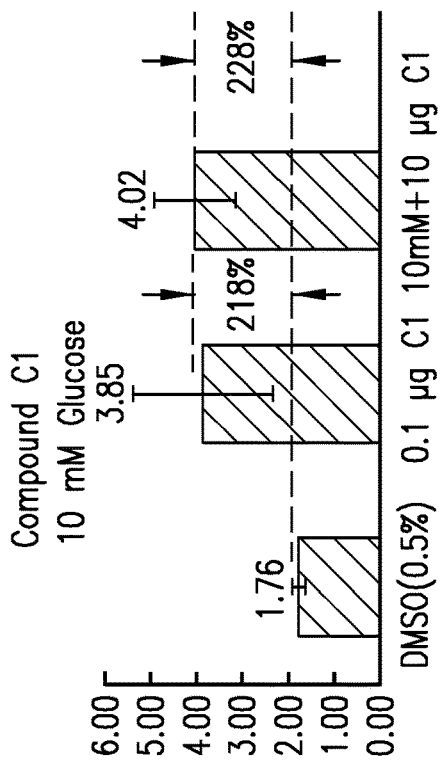
FIG. 7 is a graph illustrating insulin secretion assay results with varying amounts of compound C1 with 2 mM glucose, as set forth in Example 5.
Figure 8:
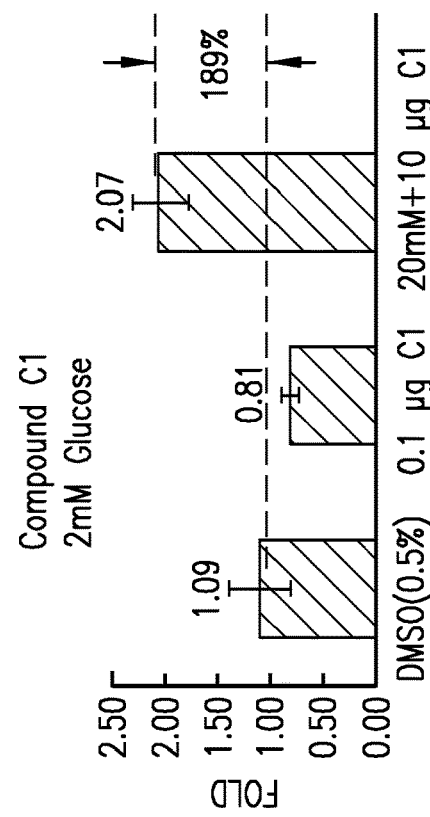
FIG. 8 is a graph illustrating insulin secretion assay results with 10 mM glucose and varying amounts of compound C1, as set forth in Example 5.
Figure 9:
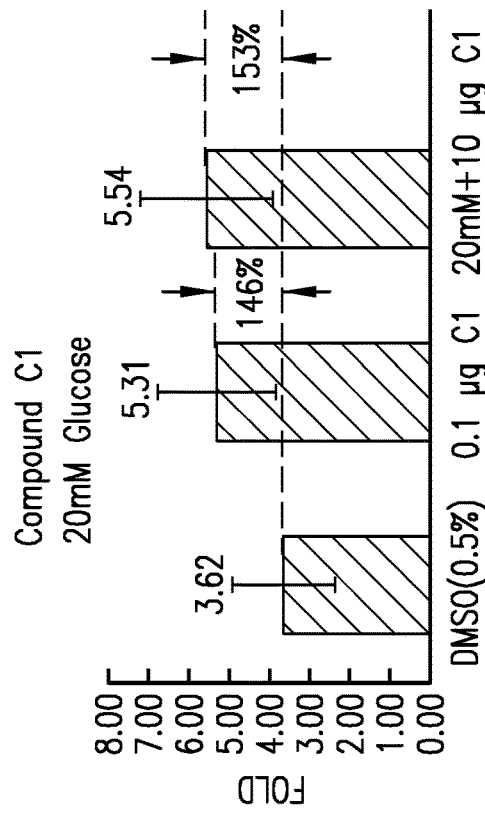
FIG. 9 is a graph illustrating insulin secretion assay results with 20 mM glucose and varying amounts of compound C1, as set forth in Example 5.
Figure 10:
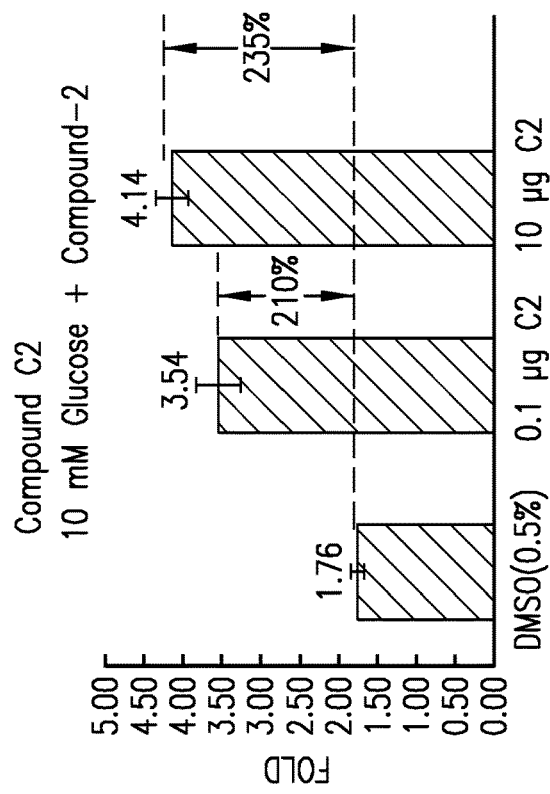
FIG. 10 is a graph illustrating insulin secretion assay results with 2 mM glucose and varying amounts of compound C2, as set forth in Example 5.
Figure 11:
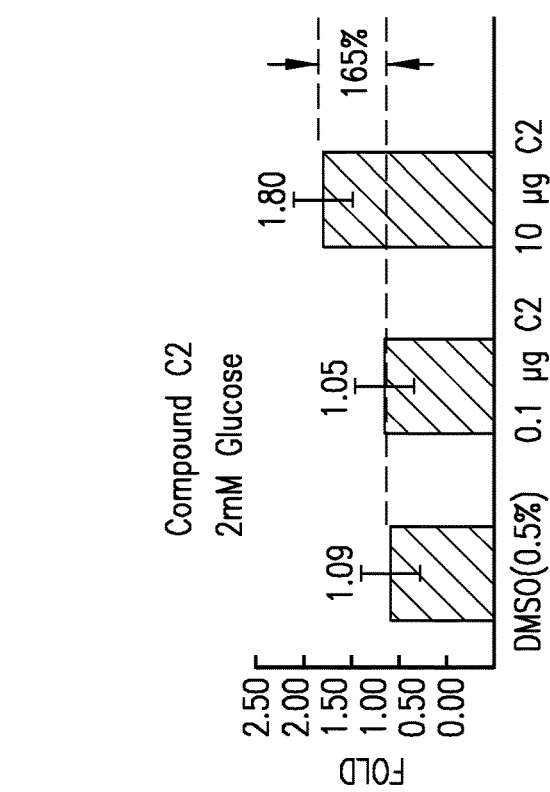
FIG. 11 is a graph illustrating insulin secretion assay results with 10 mM glucose and varying amounts of compound C2, as set forth in Example 5.
Figure 12:
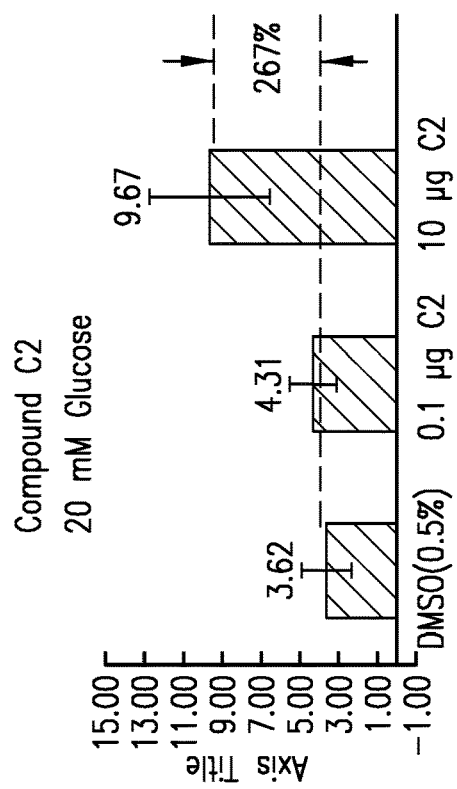
FIG. 12 is a graph illustrating insulin secretion assay results with 20 mM glucose and varying amounts of compound C2, as set forth in Example 5.

The cells were washed with KRB containing 0.1% BSA and starved for 1 hour in 2 mM glucose-KRB/BSA at 37° C. in 5% CO2. Following starvation, the cells were treated with or without the compounds at varying glucose concentrations of 2 mM, 10, mM, and 20 mM in KRB/BSA for 1 hour at 37° C. in 5% CO2. The amount of secreted mouse insulin was measured in the KRB/BSA incubation buffer using the mouse insulin ELISA kit from Mercer EXPert Assays. The cells were then lysed for protein quantification. The data presented in FIGS. 5-6 illustrate the secreted insulin test results for glucose and diazoxide, while FIGS. 7-9 (compound C1) and 10-12 (compound C2) illustrate the secreted insulin test results using C1 and C2. The data presented in FIGS. 7-12 are presented as the fold changes in the secreted insulin per milligram protein per hour, compared to the cell control.

C. Results

Concentration-dependent insulin secretion is evident upon varying the concentration of glucose with MIN-6 cells. The test compounds were evaluated at different glucose concentrations and the results showed that both compounds C1 and C2 enhanced glucose-mediated insulin secretion.

Compound C1 led to an increase of 146-228% insulin secretion. The percentage increase was higher in the range of 2-10 nM. Compound C2 showed an increase of 165-267% insulin secretion. The percentage increase was higher at the higher concentration of glucose. Diazoxide showed significant inhibition of insulin secretion.

Example 6

In this test, a glucose stimulated insulin secretion assay was performed using the MIN-6 cell line and a compound mixture of compounds VIIID and VIIIF (MW about 540), referred to as C3. The test details and assay conditions are set forth below.

A. Test Details

| | |
|---|---|
| Cell Line | MIN-6 |
| Cell Density | 3 × 10$^4$ cells/well |
| Compounds | C3 |
| | Gliclazide |
| Solvent | DMSO |
| Test Concentrations | 0.185, 1.85, and 18.5 μM |
| | Gliclazide: 100 nM |
| Cell Control | Krebs Ringer Buffer (KRB) containing 0.1% BSA (no glucose) |
| Vehicle Control | 0.5% DMSO |
| Control | Glucose + 0.5% DMSO |
| Test | Glucose + C3 in DMSO |

B. Assay Conditions

Figure 13:
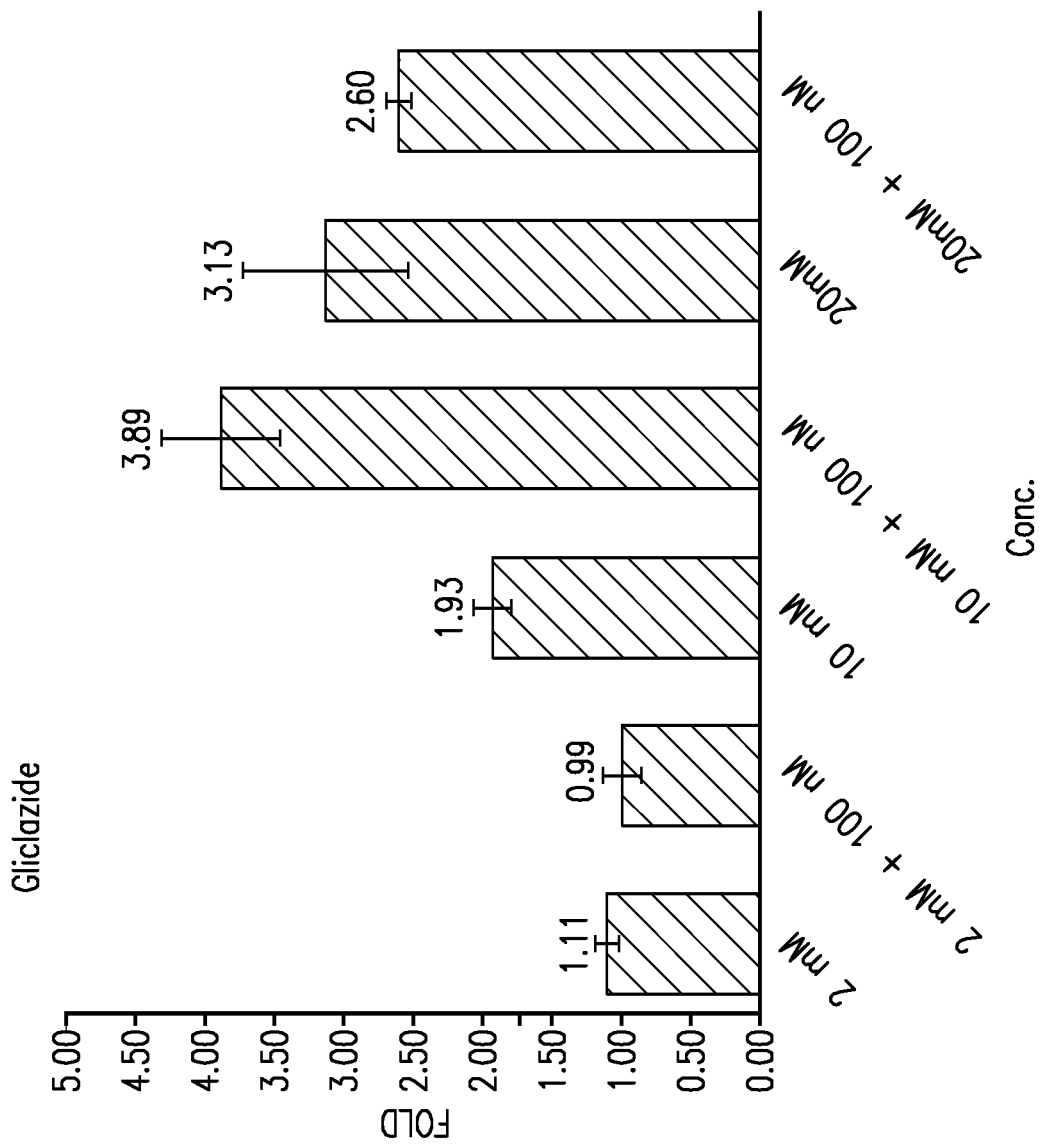
FIG. 13 is a graph illustrating insulin secretion assay results with varying amounts of glucose, with and without 100 nM gliclazide, as set forth in Example 6.
Figures 14, 15, 16:
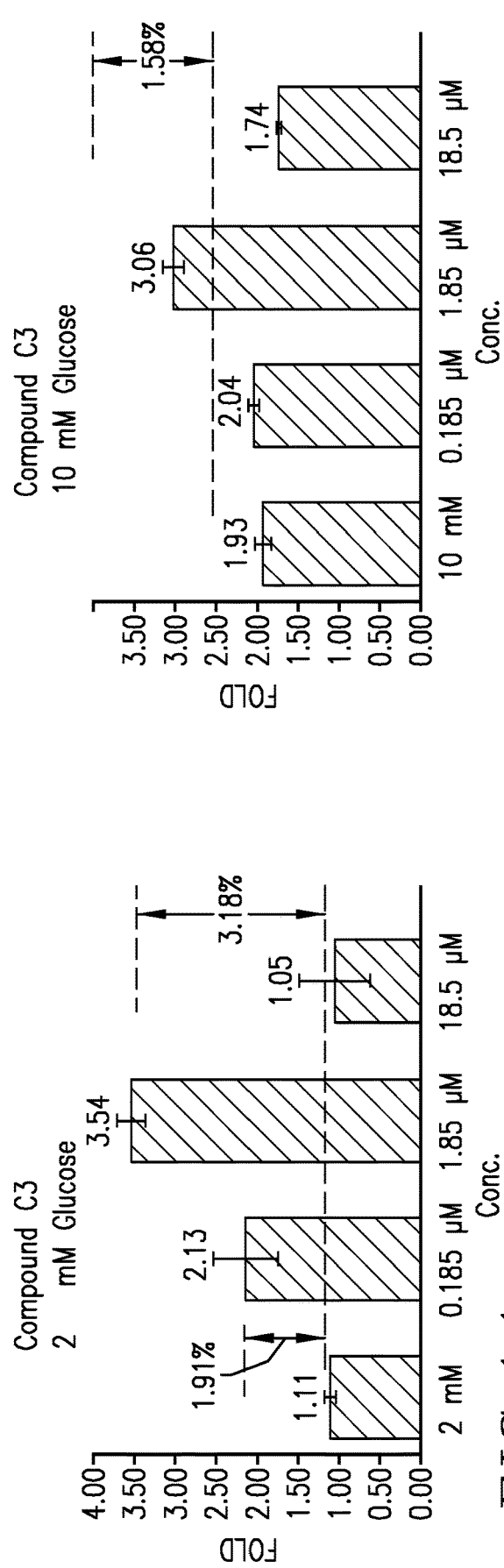
FIG. 14 is a graph illustrating insulin secretion assay results with 2 mM glucose and varying amounts of compound C3, as set forth in Example 6.
FIG. 15 is a graph illustrating insulin secretion assay results with 10 mM glucose and varying amounts of compound C3, as set forth in Example 6.
FIG. 16 is a graph illustrating insulin secretion assay results with 20 mM glucose and varying amounts of compound C3, as set forth in Example 6.

The cells were washed with KRB containing 0.1% BSA and starved for 1 hour in 2 mM glucose-KRB/BSA at 37° C. in 5% CO2. Following starvation, the cells were treated with or without the compounds at varying glucose concentrations of 2 mM, 10, mM, and 20 mM in KRB/BSA for 1 hour at 37° C. in 5% CO2. The amount of secreted mouse insulin was measured in the KRB/BSA incubation buffer using the mouse insulin ELISA kit from Mercer EXPert Assays. The cells were then lysed for protein quantification. The data is presented in FIGS. 13 (gliclazide) and 14-16 (C3) as the fold change in the secreted insulin per milligram protein per hour, compared to the cell control.

As reflected in the graphical data of FIGS. 13-16, insulin secretion is shown using varying concentrations of glucose in MIN-6 cells. Gliclazide was used as a positive control, and exhibited enhanced insulin secretion at 10 mM of glucose. Moreover, C3 enhanced glucose-mediated insulin secretion in the range of 2-10 mM of glucose and further exhibited a noticeable increase of 1.58-3.18 folds in insulin secretion. The percentage increase was highest at 2 mM glucose. C3 gave the best results in the concentration range of 0.185-1.85 µM.

Example 7

In this test, another glucose stimulated insulin secretion assay was performed using two test compounds, namely C1 (MW about 378) and C3 (MW about 540). The MIN-6 cell line was used and the test details and assay conditions are set forth below.

A. Test Details

| | |
|---|---|
| Cell Line | MIN-6 |
| Cell Density | $10^4$ cells/well |
| Compounds | C1 |
| | C3 |
| | Gliclazide |
| Solvent | DMSO |
| Test Concentrations | 0.264, 2.64, and 26.4 µM |
| | Gliclazide: 100 µM |
| Cell Control | Krebs Ringer Buffer (KRB) (no glucose) |
| Vehicle Control | 0.5% DMSO |
| Control | Glucose 2 mM and 25 mM + 0.5% DMSO |
| Test | Glucose 2 mM and 25 mM + C1 and C3 in DMSO |

B. Assay Conditions

The cells were revived and maintained in T-flasks. Upon reaching the required confluency, the cells were seeded in 96-well plates. The seeded cells were serum-starved in the presence of glucose for 30 minutes at 37° C. in 5% CO2. Following starvation, the cells were treated with or without the compounds at the varying glucose concentrations in KRB for 2 hours at 37° C. in 5% CO2. The cell supernatants were collected and tested for insulin secretion using the mouse insulin ELISA kit from Mercer EXPert Assays.

Insulin secretion was enhanced by glucose stimulation. In the presence of Gliclazide (100 µM), the enhanced insulin secretion was observed at the lower glucose concentration. At the higher glucose concentration, Gliclazide showed a saturation effect. The C1 compound demonstrated increased insulin secretion as compared with the glucose control, with a saturation effect at the higher glucose level. The C3 compound exhibited negligible enhancement of insulin secretion at all three dosage levels.

As reflected in the graphical data of FIGS. 13-16, insulin secretion is shown using varying concentrations of glucose in MIN-6 cells. Gliclazide was used as a positive control, and exhibited enhanced insulin secretion at 10 mM of glucose. Moreover, C3 enhanced glucose-mediated insulin secretion in the range of 2-10 mM of glucose and further exhibited a noticeable increase of 1.58-3.18 folds in insulin secretion. The percentage increase was highest at 2 mM glucose. C3 gave the best results in the concentration range of 0.185-1.85 µM.

While the anti-cancer properties of the compositions of the invention have been demonstrated against certain cancers, it is considered that the invention is applicable to virtually all cancers, such as the following: Acute Lymphoblastic Leukemia, Adult; Acute Lymphoblastic Leukemia, Childhood; Acute Myeloid Leukemia, Adult; Acute Myeloid Leukemia, Childhood; Adrenocortical Carcinoma; Adrenocortical Carcinoma, Childhood; Adolescents, Cancer in; AIDS-Related Cancers; AIDS-Related Lymphoma; Anal Cancer; Appendix Cancer; Astrocytomas, Childhood; Atypical Teratoid/Rhabdoid Tumor, Childhood, Central Nervous System; Basal Cell Carcinoma; Bile Duct Cancer, Extrahepatic; Bladder Cancer; Bladder Cancer, Childhood; Bone Cancer, Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Brain Tumor, Central Nervous System Embryonal Tumors, Childhood; Brain Tumor, Astrocytomas, Childhood; Brain Tumor, Craniopharyngioma, Childhood; Brain Tumor, Ependymoblastoma, Childhood; Brain Tumor, Ependymoma, Childhood; Brain Tumor, Medulloblastoma, Childhood; Brain Tumor, Medulloepithelioma, Childhood; Brain Tumor, Pineal Parenchymal Tumors of Intermediate Differentiation, Childhood; Brain Tumor, Supratentorial Primitive Neuroectodermal Tumors and Pineoblastoma, Childhood; Brain and Spinal Cord Tumors, Childhood (Other); Breast Cancer; Breast Cancer and Pregnancy; Breast Cancer, Childhood; Breast Cancer, Male; Bronchial Tumors, Childhood; Burkitt Lymphoma; Carcinoid Tumor, Childhood; Carcinoid Tumor, Gastrointestinal; Carcinoma of Unknown Primary; Central Nervous System Atypical Teratoid/Rhabdoid Tumor, Childhood; Central Nervous System Embryonal Tumors, Childhood; Central Nervous System (CNS) Lymphoma, Primary; Cervical Cancer; Cervical Cancer, Childhood; Childhood Cancers; Chordoma, Childhood; Chronic Lymphocytic Leukemia; Chronic Myelogenous Leukemia; Chronic Myeloproliferative Disorders; Colon Cancer; Colorectal Cancer, Childhood; Craniopharyngioma, Childhood; Cutaneous T-Cell Lymphoma; Embryonal Tumors, Central Nervous System, Childhood; Endometrial Cancer; Ependymoblastoma, Childhood; Ependymoma, Childhood; Esophageal Cancer; Esophageal Cancer, Childhood; Esthesioneuroblastoma, Childhood; Ewing Sarcoma Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Gastrointestinal Stromal Tumor (GIST); Gastrointestinal Stromal Cell Tumor, Childhood; Germ Cell Tumor, Extracranial, Childhood; Germ Cell Tumor, Extragonadal; Germ Cell Tumor, Ovarian; Gestational Trophoblastic Tumor; Glioma, Adult; Glioma, Childhood Brain Stem; Hairy Cell Leukemia; Head and Neck Cancer; Heart Cancer, Childhood; Hepatocellular (Liver) Cancer, Adult (Primary); Hepatocellular (Liver) Cancer, Childhood (Primary); Histiocytosis, Langerhans Cell; Hodgkin Lymphoma, Adult; Hodgkin Lymphoma, Childhood; Hypopharyngeal Cancer; Intraocular Melanoma; Islet Cell Tumors (Endocrine Pancreas); Kaposi Sarcoma; Kidney (Renal Cell) Cancer; Kidney Cancer, Childhood; Langerhans Cell Histiocytosis; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin, Adult; Lymphoma, Hodgkin, Childhood; Lymphoma, Non-Hodgkin, Adult; Lymphoma, Non-Hodgkin, Childhood; Lymphoma, Primary Central Nervous System (CNS); Macroglobulinemia, Waldenstrom; Malignant Fibrous Histiocytoma of Bone and Osteosarcoma; Medulloblastoma, Childhood; Medulloepithelioma, Childhood; Melanoma; Melanoma, Intraocular (Eye); Merkel Cell Carcinoma; Mesothelioma, Adult Malignant; Mesothelioma, Childhood; Metastatic Squamous Neck Cancer with Occult Primary; Mouth Cancer; Multiple Endocrine Neoplasia Syndromes, Childhood; Multiple Myeloma/Plasma Cell Neoplasm; Mycosis Fungoides; Myelodysplastic Syndromes; Myelodysplastic/Myeloproliferative Neoplasms; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin Lymphoma, Adult; Non-Hodgkin Lymphoma, Childhood; Non-Small Cell Lung Cancer; Oral Cancer, Childhood; Oral Cavity Cancer, Lip and; Oropharyngeal Cancer; Osteosarcoma and Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell Tumors; Papillomatosis, Childhood; Paranasal Sinus and Nasal Cavity Cancer; Parathyroid Cancer; Penile Cancer; Pharyngeal Cancer; Pineal Parenchymal Tumors of Intermediate Differentiation, Childhood; Pineoblastoma and Supratentorial Primitive Neuroectodermal Tumors, Childhood; Pituitary Tumor; Plasma Cell Neoplasm/Multiple Myeloma; Pleuropulmonary Blastoma, Childhood; Pregnancy and Breast Cancer; Primary Central Nervous System (CNS) Lymphoma; Prostate Cancer; Rectal Cancer; Renal Cell (Kidney) Cancer; Renal Pelvis and Ureter, Transitional Cell Cancer; Respiratory Tract Cancer with Chromosome 15 Changes; Retinoblastoma; Rhabdomyosarcoma, Childhood; Salivary Gland Cancer; Salivary Gland Cancer, Childhood; Sarcoma, Ewing Sarcoma Family of Tumors; Sarcoma, Kaposi; Sarcoma, Soft Tissue, Adult; Sarcoma, Soft Tissue, Childhood; Sarcoma, Uterine; Sezary Syndrome; Skin Cancer (Nonmelanoma); Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Cell Carcinoma; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Testicular Cancer, Childhood; Throat Cancer; Thymoma and Thymic Carcinoma; Thymoma and Thymic Carcinoma, Childhood; Thyroid Cancer; Thyroid Cancer, Childhood; Transitional Cell Cancer of the Renal Pelvis and Ureter; Trophoblastic Tumor, Gestational; Unknown Primary Site, Carcinoma of, Adult; Unknown Primary Site, Cancer of, Childhood; Unusual Cancers of Childhood; Ureter and Renal Pelvis, Transitional Cell Cancer; Urethral Cancer; Uterine Cancer, Endometrial; Uterine Sarcoma; Vaginal Cancer; Vaginal Cancer, Childhood; Vulvar Cancer; Waldenstrom Macroglobulinemia; Wilms Tumor; Women's Cancers.

We claim:

1. A method of preparing a reaction product compound, said method comprising mixing together thymoquinone and a harmaline tautomer comprising the structure:

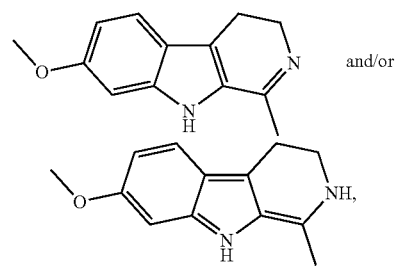

and causing said mixed reactants to react and form said reaction product compound.

2. The method of claim 1, wherein the mixing step comprises mixing together solid particulate thymoquinone with said harmaline in a non-interfering solvent, and allowing the mixture to stand for a period of time to effect said reaction and form said reaction product compound.

3. The method of claim 1, the weight ratio of thymoquinone:harmaline compound ranging from about 0.5:1 to 25:1.

4. The method of claim 2, wherein said non-interfering solvent is selected from the group consisting of C1-C4 lower alcohols, DMSO, and mixtures thereof.

5. The method of claim 2, said period of time ranging from about 12 hours-4 weeks.

6. The method of claim 1, said reaction being carried out at room temperature.

7. The method of claim 1, wherein said thymoquinone comprises the structure:

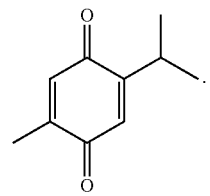

8. The method of claim 7, wherein said reaction products are isomers comprising a single thymoquinone moiety and a single harmaline moiety and having the structures:

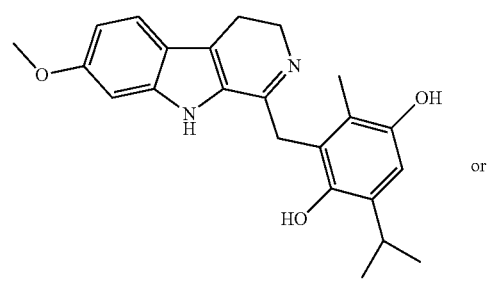

-continued
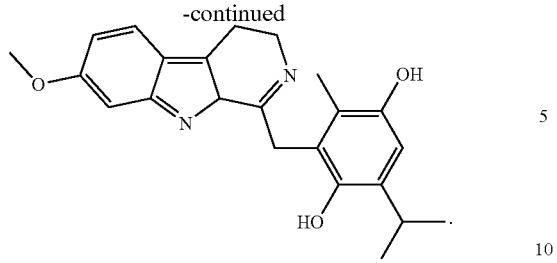
9. The method of claim 8, said reaction products having a molecular weight of approximately 378.
* * * * *